United States Patent [19]

Lam Shang Leen

[11] Patent Number: 4,623,526

[45] Date of Patent: * Nov. 18, 1986

[54] PROCESS FOR THE PREPARATION OF A CRYSTALLINE TITANOBOROSILICATE

[75] Inventor: Kee K. Lam Shang Leen, Ottawa, Canada

[73] Assignee: Centre de Recherche Industrielle du Quebec, Quebec, Canada

[ * ] Notice: The portion of the term of this patent subsequent to May 28, 2002 has been disclaimed.

[21] Appl. No.: 717,662

[22] Filed: Mar. 29, 1985

Related U.S. Application Data

[63] Continuation-in-part of Ser. No. 411,621, Aug. 26, 1982, Pat. No. 4,519,998.

[51] Int. Cl.$^4$ ............................................. C01B 35/10
[52] U.S. Cl. ................................. 423/277; 423/326; 423/328; 502/60; 502/77; 502/202; 502/239
[58] Field of Search ................. 423/277, 326; 502/202, 502/242

[56] References Cited

U.S. PATENT DOCUMENTS 4,410,501 10/1983 Taramasso et al. .................. 423/326
4,519,998 5/1985 Leen .................................... 423/277

FOREIGN PATENT DOCUMENTS 0077522  4/1983  European Pat. Off. ............ 423/328
3141283  4/1983  Fed. Rep. of Germany ...... 423/328
2024790  1/1980  United Kingdom ................ 502/202
2144727  3/1985  United Kingdom ................ 423/326

OTHER PUBLICATIONS

M. G. Howden, *Zeolites*, vol. 5, (1985), pp. 334–338.

*Primary Examiner*—John Doll
*Assistant Examiner*—Jackson Leeds
*Attorney, Agent, or Firm*—Cushman, Darby & Cushman

[57] ABSTRACT

A new crystalline titanoborosilicate comprises a molecular sieve material having the following composition in terms of mole ratios of oxide:

$$0.9 \pm 0.2 M_{2/n}O : aTiO_2 : bB_2O_3 : ySiO_2 \cdot zH_2O$$

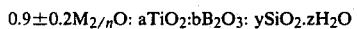

wherein M is at least one cation having a valence n, a is greater than zero but less than 1, b is greater than zero but less than 1 such that a+b=1, y is a value within the range of 8 to about 500, and z is a value within the range of 0 to about 100 and giving a specific X-ray diffraction pattern. The crystalline titanoborosilicate is used to catalyze various processes such as conversion of simple alcohols into liquid hydrocarbons having boiling points within the gasoline boiling range, aromatization, and alkylation. A process of preparing the new crystalline titanoborosilicate is also disclosed.

4 Claims, No Drawings

PROCESS FOR THE PREPARATION OF A CRYSTALLINE TITANOBOROSILICATE

This is a continuation-in-part of copending application Ser. No. 411,621 filed Aug. 26, 1982 now U.S. Pat. No. 4,519,998.

BACKGROUND OF THE INVENTION (a) Field of the Invention

This invention relates to novel crystalline titanoborosilicates and to their applications. More particularly, it relates to novel titanoborosilicate crystalline zeolitic materials possessing catalytic properties and to various conversion processes using such crystalline titanoborosilicates.

(b) Description of Prior Art

It has been demonstrated in the past that zeolitic materials, both natural and synthetic, and commonly referred to as molecular sieves, can have catalytic, sorption and separating properties. A number of existing processes such as catalytic cracking, methanol conversion, isomerization of xylenes, alkylation of aromatics, exemplify the use of these molecular sieve materials.

Typically represented by aluminosilicates, zeolites are structurally complex crystalline inorganic polymers based on an infinitely extending framework of $AlO_4$ and $SiO_4$ tetrahedra linked to each other by the sharing of oxygen atoms. This framework structure contains large and small cavities interconnected by channels. These cavities and channels which are generally uniform in size thus allowing selective adsorption of hydrocarbons, are occupied by cations and water molecules. The cations may be mobile and therefore can undergo ion exchange. In view of the mobility of the cations, it is believed that zeolitic materials are in fact solid electrolytes. The water molecules may be removed reversibly by the application of heat which in most cases effectively leaves intact a highly porous crystalline structure. As the ratio of $SiO_2$ to $Al_2O_3$ increases, the zeolitic material may become more hydrophobic. In addition to their adsorption properties, zeolites are utilized in certain catalytic processes.

In terms of composition, zeolites can be regarded as being derived from silica. The substitution of some of the silicon atoms within the crystalline framework of the silica by trivalent aluminum atoms generates an anionic site in the environments of the Al atoms so that, in order to preserve electroneutrality a cation such as that of the alkali metals or alkaline earth metals is required. Considering the fact that tetraco-ordinated aluminum atoms cannot share the same oxygen atom, it follows that y in the following emperical formula representing a typical zeolite cannot be less than 2:

$$M_{2/n}O:Al_2O_3:ySiO_2:wH_2O$$

wherein n is the valence of the cation, Y is 2 or greater and w is a number representing the water contained in the intracrystalline channel systems of the zeolite after synthesis or crystallization in nature.

Prior art developments have resulted in the synthesis of more than 150 zeolite types. To date, forty zeolite minerals are known. Synthetic crystalline aluminosilicates are the most prevalent and are usually designated in the patent literature and in the published journals by symbols or letters. Examples of some of the synthetic aluminosilicate zeolites are:

Zeolite A (U.S. Pat. No. 2,882,243);
Zeolite X (U.S. Pat. No. 2,882,244);
Zeolite Y (U.S. Pat. No. 3,130,007);
Zeolite ZSM-5 (U.S. Pat. No. 3,702,886);
Zeolite ZSM-11 (U.S. Pat. No. 3,709,979);
Zeolite ZSM-12 (U.S. Pat. No. 3,832,449);
Zeta-1 (British Pat. No. 1,553,209).

U.S. Pat. No. 3,702,886 which is here considered relevant discloses the crystalline aluminosilicate ZSM-5 and the process of preparing the same. This patent shows the preparation of a crystalline aluminosilicate and a crystalline gallosilicate by reacting a silicon oxide with aluminum oxide or germanium oxide in a range of specific ratios under specified reaction conditions. The product obtained has a specified X-ray diffraction pattern. This patent is therefore limited to alumino or gallosilicates. Patents disclosing the synthesis of ZSM-11 and ZSM-12 are likewise limited in scope to crystalline alumino or gallosilicates which also provide specified X-ray diffraction patterns.

The production of the ZSM materials makes use of a mixed base system wherein sodium aluminate and a silicon-containing material are allowed to react in the presence of sodium hydroxide and an organic base template such as tetrapropylammonium hydroxide or tetrapropylammonium bromide under specified reaction conditions to yield the crystalline aluminosilicates.

U.S. Pat. No. 3,328,119 which is considered relevant art to this invention claims and teaches the process of preparation of a crystalline aluminosilicate wherein boria forms an integral part of the crystal framework structure of the zeolite material.

Another U.S. Pat. No. 4,269,813 which is considered relevant to this invention discloses a class of crystalline borosilicates designated AMS-1B and a process for preparing the same.

Additional relevant prior art comprises U.S. Pat. Nos. 3,329,480; 3,329,481; 4,029,716; 4,078,009; German Pat. No. 2,830,787. U.S. Pat. Nos. 3,329,480 and 3,329,481 relate to titanosilicates and zirconosilicates respectively. U.S. Pat. Nos. 4,029,716 and 4,078,009 relate to a crystalline aluminosilicate zeolite having a silica-to alumina ratio of at least 12 and a constraint index.

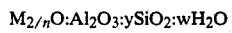

$$\frac{\log_{10}(\text{fraction of n-hexane remaining})}{\log_{10}(\text{fraction of 3-methylpentane remaining})}$$

within the range of 1 to 12 and containing boron in an amount of at least 0.2 weight percent as a result of the reaction of the zeolite with a boron-containing compound.

German Pat. No. 2,830,789 relates to crystalline alumino, boro, arseno, and antimony silicates having specified X-ray diffraction patterns and to processes for preparing the same.

SUMMARY OF THE INVENTION

The present invention relates to a novel family of stable synthetic crystalline titanoborosilicates identified as ZMQ-TB and possessing a specific X-ray diffraction pattern. It is understood that the titanium and boron constitute an inherent part of the crystal framework structure of the material rather than a subsequent modification of the material composition.

The ZMQ-TB crystalline titanoborosilicate according to the invention are prepared by reacting the product formed as a result of a reaction between a titanium-containing material and an alkali tetrahydroborate with a silicon-containing material in a basic medium, which contains an alkali hydroxide or an alkaline earth hydroxide and an alkylammonium ion and/or a mineralizing agent, such as sodium chloride. Those skilled in the art would appreciate that the reactions between a titanium-containing material and an alkali tetrahydroborate are still obscure. However, it is believed that $Ti^{IV}$ is reduced to $Ti^{III}$.

The zeolite product formed, ZMQ-TB, following hydrothermic treatment is crystallized out from the titanium and boron containing mixture with the titanium and boron already contained within the crystal framework prior to physical separation of the product from the mother liquor. It will be understood that any modification of the crystallized titanoborosilicate zeolite subsequent to its formation using such techniques as metal impregnation or deposition, cation exchange is to be clearly distinguished from the process of the present invention.

Broadly speaking, according to the present invention, there is provided crystalline titanoborosilicate product which comprises a molecular sieve material having the following composition in terms of mole ratios of oxides:

$$0.9 \pm 0.2 M_{2/n}O : aTiO_2 : bB_2O_3 : ySiO_2 . zH_2O$$

wherein M is selected from the group comprising hydrogen, ammonium, monovalent and divalent metal cations and mixtures thereof; n is the valence of M; a is greater than zero but less than 1, b is greater than zero but less than 1, such that a+b=1, y has a value between about 8 and about 500 and z is a value between 0 and 100.

DESCRIPTION OF PREFERRED EMBODIMENTS

In accordance with a preferred embodiment of the invention, such crystalline titanoborosilicate provides an X-ray powder diffraction pattern which comprises the following X-ray diffraction lines as shown below:

| Interplanar spacing d (A) | Relative intensity |
| --- | --- |
| 15.5 ± 0.2* | MS-VS |
| 11.1 ± 0.2 | W-S |
| 10.05 ± 0.2 | W-MS |
| 5.18 ± 0.05 | VW-M |
| 4.11 ± 0.05 | M-VS |
| 3.83 ± 0.05 | M-VS |
| 3.71 ± 0.05 | MS |
| 3.64 ± 0.05 | M-MS |
| 3.45 ± 0.05* | MS-VS |
| 3.31 ± 0.05 | M-S |
| 3.15 ± 0.05* | M-S |
| 2.98 ± 0.02 | VW-M |
| 2.50 ± 0.02 | VW-M |
| 1.99 ± 0.02 | VW-M |

*The three peaks are probably due to the presence of magadiite presumably formed in the presence of high concentration of salts namely sodium chloride.

These data were obtained by standard X-ray diffraction technique using the k-alpha doublet of copper radiation. The relative intensities, were calculated from the relation 100 $I/I_o$, where $I_o$ is the intensity of the strongest line and I is the intensity of each peak height measured. In the results given above and in Table I which gives a more detailed analysis the relative intensities are given in terms of the symbols:

VS = very strong;
S = strong;
MS = medium strong;
M = medium;
MW = medium weak;
W = weak;
VW = very weak.

TABLE I

| Interplanar spacing d (A) | Relative intensity |
| --- | --- |
| 15.5 ± 0.2* | MS-VS |
| 11.1 ± 0.2 | W-S |
| 10.05 ± 0.2 | W-MS |
| 7.76 ± 0.15 | W |
| 7.37 ± 0.15 | VW |
| 6.71 ± 0.1 | VW |
| 6.38 ± 0.1 | W |
| 6.02 ± 0.1 | W |
| 5.68 ± 0.1 | W |
| 5.54 ± 0.1 | W |
| 5.18 ± 0.1 | W |
| 5.04 ± 0.1 | VW |
| 4.61 ± 0.08 | VW |
| 4.34 ± 0.08 | W |
| 4.23 ± 0.08 | W |
| 4.11 ± 0.05 | VS |
| 3.83 ± 0.05 | VS |
| 3.71 ± 0.05 | M-S |
| 3.64 ± 0.05 | M-S |
| 3.56 ± 0.05 | W-M |
| 3.45 ± 0.05* | VS |
| 3.31 ± 0.05 | M-S |
| 3.15 ± 0.05* | S |
| 3.05 ± 0.05 | VW |
| 2.98 ± 0.02 | W |
| 2.94 ± 0.02 | VW |
| 2.85 ± 0.02 | VW |
| 2.83 ± 0.02 | VW |
| 2.72 ± 0.02 | VW |
| 2.64 ± 0.02 | VW |
| 2.59 ± 0.02 | VW |
| 2.51 ± 0.02 | W |

*probably due to magadiite

It will be understood that the above X-ray diffraction pattern generally applies to all the species of ZMQ-TB compositions. Minor shifts in interplanar spacings and minor variations in relative intensity may occur as a result of ion exchange of sodium ions with other cations and of heat treatment, but on the whole the diffraction pattern will substantially be the same.

The present invention therefore relates to a novel synthetic crystalline molecular sieve material constituted by a crystalline titanoborosilicate. The family of such crystalline borosilicate materials, which are identified as ZMQ-TB titanoborosilicate, possesses a characteristic X-ray diffraction pattern as is shown in the various tables hereinafter. Such crystalline titanoborosilicates can generally be represented in terms of the mole ratios of oxides by Equation 1:

EQUATION 1

$$0.9 \pm 0.2 M_{2/n}O : aTiO_2 : bB_2O_3 : ySiO_2 . zH_2O$$

wherein M is at least one cation of valence n, a is greater than zero but less than 1, b is greater than zero but less than 1, such that a+b=1, y is a number between 8 and 500 and z is a number between 0 and 100.

In another instance, the crystalline titanoborosilicate according to the invention which is not yet activated or calcined at high temperatures can be generally represented in terms of the mole ratios of oxides by Equation 2.

EQUATION 2

$$0.9 \pm 0.2[xR_2O + (1-x)M_{2/n}O] : aTiO_2 : bB_2O_3 : ySiO_2 \cdot zH_2O$$

wherein R is an alkylammonium cation, M is at least one cation of valence n, a is greater than zero but less than 1, b is greater than zero but less than 1, such that a+b=1, y is a number between 8 and 500, z is a number between 0 and 100, and x is greater than 0 but less than 1.

In Equation 1, M can be an alkali metal cation, an alkaline earth metal cation, a hydrogen cation, an ammonium cation, an alkylammonium cation, a catalytically active metal cation or mixture thereof.

In Equation 2, M can be an alkali metal cation, an alkaline earth metal cation, a hydrogen cation, an ammonium cation, a catalytically active metal cation or mixture thereof. Table II summarizes the values that y can take:

TABLE II

| y | BROAD | SUITABLE | PREFERRED | MORE PREFERRED |
|---|---|---|---|---|
| | 8–500 | 8–300 | 50–160 | 60–120 |

Preferably z in Equation 2 is within the range of 0 to about 40.

In the general formulations represented by the above equations M can be substituted at least in part by other cations using such techniques well known in the art, for example, ion exchange. These cations are preferably those which render ZMQ-TB catalytically active especially in the conversion of hydrocarbons. Such cations or mixtures thereof include metals from Groups IB, IIB, VIII, Al, rare earths metals, hydrogen, noble metals and other catalytically active metals known to the art. They can constitute anywhere from about 0.05 to about 25 weight percent of the ZMQ-TB crystalline titanoborosilicate.

An X-ray powder diffraction pattern of ZMQ-TB using the Cu k-alpha radiation and indicating the significant lines are shown in Table III, which gives values that are characteristics of ZMQ-TB crystalline titanoborosilicate having the oxide mole formula given in Equation 1, which crystalline titanoborosilicate has been calcined at 538° C. for 5 hours in order to remove the tetraalkylammonium ion.

TABLE III

| Interplanar spacing d (A) | Relative intensity |
|---|---|
| 11.1 ± 0.2 | S |
| 10.05 ± 0.2 | MS |
| 7.76 ± 0.15 | W |
| 7.37 ± 0.15 | VW |
| 7.71 ± 0.1 | VW |
| 6.71 ± 0.1 | VW |
| 6.38 ± 0.1 | W |
| 6.02 ± 0.1 | W |
| 5.68 ± 0.1 | W |
| 5.54 ± 0.1 | W |
| 5.68 ± 0.1 | W |
| 5.18 ± 0.1 | W |
| 5.04 ± 0.1 | VW |
| 5.61 ± 0.08 | VW |
| 4.34 ± 0.08 | W |
| 4.23 ± 0.08 | W |
| 4.11 ± 0.05 | VS |
| 3.83 ± 0.05 | VS |
| 3.71 ± 0.05 | M-S |
| 3.64 ± 0.05 | M-S |
| 3.56 ± 0.05 | MW |
| 3.45 ± 0.05* | VS |
| 3.31 ± 0.05 | MS |
| 3.15 ± 0.05* | S |
| 3.05 ± 0.05 | VW |
| 2.98 ± 0.02 | W |
| 2.94 ± 0.02 | VW |
| 2.85 ± 0.02 | VW |
| 2.83 ± 0.02 | VW |
| 2.72 ± 0.02 | VW |
| 2.64 ± 0.02 | VW |
| 2.59 ± 0.02 | VW |
| 2.51 ± 0.02 | W |

*probably due to magadiite

Table IV presents the more significant interplanar spacings and their relative intensities.

TABLE IV

| Interplanar spacing d (A) | Relative intensity |
|---|---|
| 11.1 ± 0.2 | S |
| 10.05 ± 0.2 | MS |
| 4.11 ± 0.05 | VS |
| 3.83 ± 0.05 | VS |
| 3.71 ± 0.05 | MS |
| 3.64 ± 0.05 | M |
| 3.45 ± 0.05* | S |
| 3.31 ± 0.05 | MS |
| 3.15 ± 0.05* | S |

*probably due to magadiite

Table V presents the X-ray diffraction pattern of a ZMQ-TB titanoborosilicate, represented by Equation 2 and which has been dried at 165° C. after being separated from the mother liquor by filtration and washed copiously with water. This pattern shows the following significant lines.

TABLE V

| Interplanar spacing d (A) | Relative intensity |
|---|---|
| 11.1 ± 0.2 | MW |
| 10.0 ± 0.2 | MW |
| 5.19 ± 0.2 | W |
| 4.11 ± 0.05 | VS |
| 3.83 ± 0.05 | VS |
| 3.71 ± 0.05 | M |
| 3.64 ± 0.05 | M |
| 3.45 ± 0.05* | VS |
| 3.31 ± 0.05 | MS |
| 3.15 ± 0.05* | S |

*probably due to magadiite

The ZMQ-TB crystalline titanoborosilicate is prepared by the method which comprises:

(1) preparing a mixture consisting of the integral reaction products between a titanium-containing compound and an alkali tetrahydroborate, sodium silicate, an alkylammonium cation or a precursor of an alkylammonium cation, a mineralization agent such as sodium chloride and water. Oxides of silicon such as silicic acid and stabilized polymer of silicic acid (Ludox TM or Nalcoag TM) can also be used in place of sodium silicate, in which case, a hydroxide of an alkali metal or an alkaline earth metal or mixture thereof is used;

(2) maintaining said mixture at suitable reaction conditions to effect formation of said titanoborosilicate, said reaction conditions preferably including a reaction temperature between 25° C. to about 300° C., a pressure of at least the vapour pressure of water at said reaction temperature, and a reaction time sufficient to effect crystallization of said titanoborosilicate.

Examples of alkali tetrahydroborates are sodium tetrahydroborate, potassium tetrahydroborate and lithium tetrahydroborate. Examples of alkylammonium cations are tetrapropylammonium bromide, tetrapropylammonium hydroxide and a precursor of said cations such as an alkylamine, an alkylamine plus an alkyl halide. Tetrapropylammonium bromide can be prepared in situ by reacting stoichiometric amounts of tri-n-propylamine and n-bromopropane.

The mixture used in the method of preparation of ZMQ-TB titanoborosilicate can be further characterized in terms of mole ratios of oxides in the ranges presented in Table VI.

TABLE VI

|  | BROAD | PREFERRED | MOST PREFERRED |
|---|---|---|---|
| $\frac{SiO_2}{B_2O_3}$ | 8–400 | 10–175 | 10–100 |
| $\frac{SiO_2}{TiO_2}$ | 8–400 | 10–75 | 10–100 |
| $OH^-/SiO_2$ | 0.01–11 | 0.1–2 | 0.1–1 |
| $\frac{R_2O}{(R_2O + M_{2/n}O)}$ | 0.1–1 | 0.2–0.97 | 0.3–0.97 |
| $H_2O/OH^-$ | 10–4000 | 10–500 | 10–500 | wherein R is an alkylamine or alkylammonium cation, preferably tetra-n-propyl ammonium cation, M is at least one cation of valence n such as an alkali-metal or an alkaline-earth metal cation.

When an alkali metal hydroxide is used in the preparation to provide a source of alkali metal ions for electrovalent neutrality and to control the pH of the reaction mixture, the values of the ratio of $OH^-/SiO_2$ in Table VI should be such as to render the pH of the system broadly within the range of about 9 to about 13.5. An alkaline pH within that range favours the formation of crystalline ZMQ-TB titanoborosilicate. The pH of the system falling within the range of about 10.5 to 11.5 is to be preferred as it favours the incorporation of titanium and boron into the framework structure of the molecular sieve.

Each ingredient should be added in an amount calculated to give the desired molar composition in the resulting mixture. For example, by regulating the amount of boron (represented by $B_2O_3$) and titanium (represented by $TiO_2$) in the reaction mixture, the $SiO_2/B_2O_3$ and $SiO_2/TiO_2$ molar ratios in the final product can vary within the ranges shown in Table VI. In view of the fact that commercially available materials utilized in the preparation of the titanoborosilicate do contain very minor amounts of aluminium, the molar ratios of $SiO_2/Al_2O_3$ in the titanoborosilicate can vary anywhere from 1000 onwards.

Reaction conditions conducive to the formation of crystalline titanoborosilicate preferably include heating the reaction mixture from about 25° C. to 300° C. for a period ranging from less than 24 hours to 4 weeks under autogeneous pressure. Especially preferred reaction conditions include a temperature around 160° C. for a period about a week. It is generally considered that the formation of zeolites requires low temperatures, hydrothermal conditions with concurrent low autogeneous pressure at saturated water vapour pressure and a high degree of supersaturation of the gel components thereby leading to the nucleation of a large number of crystals. Generally, the presence of a relatively high amount of sodium chloride aids in the mineralization of zeolite.

Calcination of crystalline titanoborosilicate washed free of soluble salts is carried out in air at temperatures anywhere from 260° C. to 590° C. Although said crystalline titanoborosilicate is highly thermally stable, it is advisable not to calcine them at extreme temperatures because of the risk of modifying its structure or of causing total breakdown of its structure, thereby leading to the formation of allotropic forms of silica. Preferably, the calcination temperature required to remove the alkylammonium cation from the "as made" crystalline material need not exceed 540° C. The hydrogen form of crystalline ZMQ-TB is prepared by treating the calcined material with an aqueous solution of 5M $NH_4Cl$ at 100° C. under autogeneous pressure for a period varying anywhere from 1 hour to 24 hours. Ammonium nitrate and ammonium acetate can also be used in ammonium exchange. Preferably, a second treatment with fresh ammonium ion is required under the same conditions except that the period of treatment is reduced. Then it is washed free of soluble salt with water and dried at 110° C. after which it is calcined in air at 540° C. for a period varying anywhere from 3 hours to 10 hours in order to produce the hydrogen form of crystalline ZMQ-TB. This form of crystalline ZMQ-TB is particularly suitable for the conversion of methanol into liquid hydrocarbons and various conversions of hydrocarbons in general.

The crystalline titanoborosilicate can be modified for certain applications in hydrocarbon conversions by impregnation or ion exchange techniques well known in the art. It may suitably be composited with certain inorganic materials which include active and inactive materials for organic conversion processes. Examples of inorganic materials are clays, silica and/or metal oxides such as alumina, silica-alumina, silica-magnesia, silica-zirconia, etc. The matrix can be in the form of a cogel, which subsequently provides a porous matrix material. The final composite may contain between 5 to 60 wt percent crystalline ZMQ-TB.

There is also provided a process for the conversion of simple alcohols such as methanol and ethanol into liquid hydrocarbons having boiling points within the boiling range of gasoline, which process involves contacting feedstocks in vapour phase or their dehydration products equally in vapour phase with the ZMQ-TB crystalline titanoborosilicate, preferably in the H-form. The crystalline titanoborosilicate of the present invention, which possesses shape-selective catalytic properties, is also suitable for various hydrocarbon conversions such as isomerization, alkylation, aromatization and hydroisomerization.

The present invention will be further understood by the following examples, which are given for illustrative purposes only and are thus not intended to limit the scope of the invention.

EXAMPLE I

General procedures:

A solution of (1) sodium tetrahydroborate containing 28.57 weight percent B was added to a solution comprising of (2) titanium potassium oxalate containing 22.56 wt percent $TiO_2$, 26.59 wt percent $K_2O$ and 10.16 wt percent H$_2$O and sodium chloride. The resulting solution was immediately added to (3)a commercially available aqueous solution of sodium silicate containing 29.5 wt percent SiO$_2$ and 9.16 wt percent Na$_2$O under rapid stirring conditions at room temperature i.e. 25° C. After the pH of the reaction mixture had been adjusted to between 10.5–11.5, the reaction mixture was allowed to stand for a period that was sufficient to allow complete gelation. The reaction mixture was placed in an autoclave to which was subsequently added a stoichiometric mixture of n-bromopropane and tri-n-propylamine, which acted as precursor to tetrapropylammonium ion under subsequent reaction conditions. The resulting reaction mixture was continuously stirred to promote uniform dispersion of the organic phase. The temperature was raised to 158° C. and held at this temperature for a period of about 7 days or until such time as is required to effect crystallization under autogeneous pressure. At the end of this period, the solid product was allowed to cool to room temperature, filtered, and washed copiously with water to remove the soluble salts. A portion of this product was dried at about 160° C. in a forced air oven and subjected to X-ray diffraction analysis. The X-ray diffraction lines and their relative intensities are presented in Table I. Another portion washed free of soluble salts and calcined in air at 538° C. for 10 hours produced an X-ray diffraction pattern which comprised the diffraction lines and their relative intensities as presented in Table III.

EXAMPLE II

This example illustrates the synthesis of ZMQ-TB crystalline titanoborosilicate. 10 g K$_2$TiO(C$_2$O$_4$)$_2$.2H$_2$O and 145 g NaCl were dissolved in 200 g of deionized water containing 12 ml of concentrated sulfuric acid (solution I). 5 g sodium tetrahydroborate were dissolved in 100 g of deionized water (solution II). 385 g of sodium silicate (Brand 'O' of National Silicates Limited) containing 29.5 wt percent SiO$_2$ and 9.16 wt percent Na$_2$O were mixed with 850 g water (solution III). Solution II was added to solution I, followed quickly by solution III with vigorous stirring. When gelation was complete, the contents (pH 10.9) were transferred to an autoclave. 51.6 g of tri-n-propylamine and 44.4 g 1-bromopropane were added and dispersed in the reaction mixture by stirring. The temperature was raised to 158° C. and held at this value for 5 days or more to effect the crystallization of the titanoborosilicate under autogeneous pressure. At the end of this period, the contents were allowed to cool to room temperature. The resulting solid product was separated by filtration. A portion of the product was copiously washed with water to remove soluble salts and dried at 160° C. before being submitted to X-ray diffraction analysis. It was identified as crystalline ZMQ-TB titanoborosilicate.

Another washed portion of the solid product was first dried at about 160° C. in a forced air oven and then calcined at 538° C. in air for 10 hours. The X-ray diffraction lines provided by the calcined products are shown in Table III. The chemical analysis of the calcined sample gave the following results:

| | |
|---|---|
| Wt percent SiO$_2$ | 91.85 |
| Wt percent TiO$_2$ | 1.68 |
| Wt percent Na$_2$O | 4.04 |
| Wt percent B$_2$O$_3$ | 0.89 |
| Wt percent Al$_2$O$_3$ | 0.08 |

| -continued | |
|---|---|
| Wt percent volatiles | 1.46 |
| $\dfrac{SiO_2}{TiO_2}$ | 73 |
| $\dfrac{SiO_2}{B_2O_3}$ | 120 |
| $\dfrac{SiO_2}{TiO_2 + B_2O_3}$ | 45 |
| $\dfrac{Na_2O}{TiO_2 + B_2O_3}$ | 2 |
| $\dfrac{SiO_2}{Al_2O_3}$ | 1948 |

EXAMPLE III

A solution (A) containing 94,6 g tetrapropylammonium bromide, 7,2 g sodium hydroxide and 500 g water was prepared. 3,75 g sodium tetrahydroborate dissolved in 50 g water was added to a solution made up of 2,5 g K$_2$TiO(C$_2$O$_4$). 2H$_2$O and 75 g water. This constituted solution B. Solutions A and B were simultaneously added to 120 g of Nalcoag TM 1030 (30 wt percent colloidal SiO$_2$) in 100 g water under vigorous stirring conditions.

The resulting reaction mixture was placed in an autoclave. The temperature was raised to 165° C. and held at this value for 6 days to allow crystallization of the molecular sieve material. The autoclave was then allowed to cool to room temperature and the solid product was filtered and washed free of soluble salts with water. A portion of the solid product was dried at 160° C. and subjected to X-ray diffraction analysis. The product was identified as ZMQ-TB crystalline titanoborosilicate having an X-ray diffraction pattern shown in Table VII which does not include the peaks attributed to magadiite.

EXAMPLE IV

In this example, the ZMQ-TB crystalline titanoborosilicate of Example II was used to produce a catalyst capable of converting methanol and ethanol into liquid hydrocarbons.

The material from Example II was washed free of soluble salts and calcined in air at 375° C. for 15 hours to remove the organic base. The calcined molecular sieve was then exchanged twice with 5M NH$_4$Cl solution at 100° C. under autogeneous pressure, the first exchange lasting 12 hours and the second exchange lasting 5 hours. 15 ml of 5M NH$_4$Cl solution were used for each g of material used. After filtering and washing the ammonium form of the material free of chloride, it was converted into the hydrogen form by calcination in air at 538° C. for 10 hours, using a heating rate of 1° C. per minute. The product was allowed to cool at the rate of 1° C./minute to room temperature.

A portion of the catalyst was charged into an essentially adiabatic conversion reactor. Methanol vapour was first introduced into an essentially first stage adiabatic reactor containing a dehydration catalyst maintained at a temperature of 350° C. to yield an equilibrium mixture of dimethylether and methanol, which mixture was then contacted with the catalyst at 370° C. Analysis by gas chromatography of the condensed organic liquid product using an SE 30 on chromosorb W column showed that there was essentially no difference between the chromatogram obtained and that of non-leaded premium gasoline.

The organic liquid product obtained from ethanol after conversion did not show any substantial difference from that obtained from methanol due to the shape-selective property of the catalyst.

TABLE VII

| Interplanar spacing d (A) | Relative intensity |
|---|---|
| 11.1 ± 0.2 | MS-S |
| 9.9 ± 0.2 | M-S |
| 8.8 ± 0.2 | VW-W |
| 7.35 ± 0.15 | VW-W |
| 6.95 ± 0.15 | VW-W |
| 6.59 ± 0.1 | VW-W |
| 6.31 ± 0.1 | W |
| 5.97 ± 0.1 | W |
| 5.54 ± 0.1 | W |
| 5.50 ± 0.1 | W |
| 5.26 ± 0.1 | VW-W |
| 5.06 ± 0.1 | VW-W |
| 4.95 ± 0.1 | VW-W |
| 4.58 ± 0.08 | W |
| 4.40 ± 0.08 | VW-W |
| 4.30 ± 0.08 | W |
| 4.22 ± 0.08 | W |
| 3.96 ± 0.05 | W |
| 3.80 ± 0.05 | S-VS |
| 3.70 ± 0.05 | S-VS |
| 3.63 ± 0.05 | MS-S |
| 3.40 ± 0.05 | W |
| 3.29 ± 0.05 | W |
| 3.27 ± 0.05 | W |
| 3.21 ± 0.05 | VW |
| 3.10 ± 0.05 | VW |
| 3.03 ± 0.05 | W |
| 2.96 ± 0.02 | W-M |
| 2.91 ± 0.02 | W |
| 2.84 ± 0.02 | VW |
| 2.76 ± 0.02 | VW |
| 2.70 ± 0.02 | VW-W |
| 2.58 ± 0.02 | W |
| 2.46 ± 0.02 | W |
| 2.375 ± 0.02 | VW |
| 1.983 ± 0.02 | W |
| 1.975 ± 0.02 | W |
| 1.936 ± 0.02 | VW |
| 1.897 ± 0.02 | VW |
| 1.648 ± 0.02 | VW |
| 1.475 ± 0.02 | VW |
| 1.448 ± 0.02 | VW |
| 1.436 ± 0.02 | VW |
| 1.420 ± 0.02 | VW |
| 1.379 ± 0.02 | VW |

We claim:

1. A method for preparing a crystalline titanoborosilicate molecular sieve material having a composition in terms of mole ratios of oxides as follows:

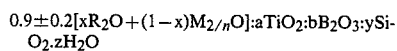

$0.9 \pm 0.2[xR_2O+(1-x)M_{2/n}O]:aTiO_2:bB_2O_3:ySiO_2.zH_2O$ wherein R is an alkylammonium cation, M is at least one cation of valence n selected from the group consisting of alkali metal or alkaline earth metal, a is greater than zero but smaller than 1, b is greater than zero but smaller than 1, such that $a+b=1$, y is a value of at least 8 up to 500, z is between 0 and 100 and x is a value greater than zero but less than 1, said material being further characterized by an X-ray diffraction pattern comprising the following diffraction lines and their relative intensities:

| Interplanar spacing d (A) | Relative intensity |
|---|---|
| 11.1 ± 0.2 | W-S |
| 10.05 ± 0.2 | W-MS |
| 5.18 ± 0.05 | VW-M |
| 4.11 ± 0.05 | M-VS |
| 3.83 ± 0.05 | M-VS |
| 3.71 ± 0.05 | MS-VS |
| 3.64 ± 0.05 | MS-S |
| 3.31 ± 0.05 | W-S |
| 2.98 ± 0.02 | VW-M |
| 2.50 ± 0.02 | VW-M |
| 1.99 ± 0.02 | VW-M | which method comprises:
  (a) providing a reaction mixture comprising:
    (1) a titanium-oxide containing material and an alkali tetrahydroborate,
    (2) sodium silicate,
    (3) an alkylammonium cation or a precursor thereof, and,
    (4) water, and
  (b) maintaining said reaction mixture under alkaline pH, at a reaction temperature between 25° C. to about 300° C., and for a time sufficient to effect formation of said crystalline titanoborosilicate under autogeneous pressure at the reaction temperature, the composition of the reaction mixture in (a) being such as to provide mole ratios in the following ranges:

| | |
|---|---|
| $R_2O(R_2O + M_{2/n}O)$ | 0.2-0.97 |
| $H_2O/OH^-$ | 10-4000 |
| $SiO_2/B_2O_3$ | 8-4000 |
| $SiO_2/TiO_2$ | 8-400. |

2. The method of claim 1 wherein the reaction temperature is between about 90° C. to about 250° C.

3. The method of claim 1 which includes the further step of calcining the crystalline titanoborosilicate at a temperature between 260° C. to 600° C.

4. The method which comprises exchanging the crystalline titanoborosilicate of claim 1 with ammonium ion followed by calcination at a temperature between 260° C. to about 600° C. to yield the hydrogen form of crystalline titanoborosilicate.

* * * * *